US00PP35174P2

(12) United States Plant Patent
Bergman

(10) Patent No.: US PP35,174 P2
(45) Date of Patent: May 16, 2023

(54) ***CHRYSANTHEMUM* PLANT NAMED 'CIDZ0115'**

(50) Latin Name: ***Chrysanthemum* x *morifolium***
Varietal Denomination: CIDZ0115

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/972,729

(22) Filed: Oct. 25, 2022

(51) Int. Cl.
*A01H 5/02* (2018.01)
*A01H 6/14* (2018.01)

(52) U.S. Cl.
USPC ..... Plt./291
CPC ..... *A01H 6/1424* (2018.05)

(58) Field of Classification Search
USPC ..... Plt./263.1, 284, 286, 287, 291
See application file for complete search history.

*Primary Examiner* — Karen M Redden
(74) *Attorney, Agent, or Firm* — Dale Skalla

(57) ABSTRACT

A new *Chrysanthemum* plant named 'CIDZ0115' particularly distinguished by its large sized lavender-pink double type inflorescences, compact strong and uniform plant habit, and a flowering response time of 7.5 weeks.

1 Drawing Sheet

Figure 1:
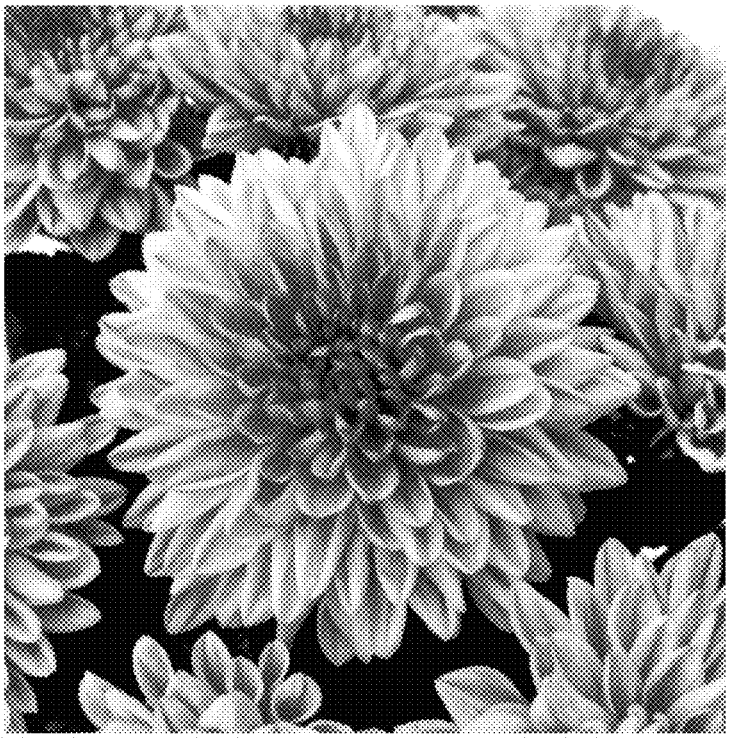

Latin name of the genus and species of the plant claimed: *Chrysanthemum* x *morifolium.*

Varietal denomination: 'CIDZ0115'.

BACKGROUND OF THE NEW PLANT

The present invention comprises a new *Chrysanthemum*, botanically known as *Chrysanthemum* x *morifolium*, and hereinafter referred to by the variety name 'CIDZ0115'.

'CIDZ0115' is a product of a planned breeding program. The new cultivar has large sized lavender-pink double type inflorescences, compact strong and uniform plant habit, and a flowering response time of 7.5 weeks.

'CIDZ0115' originated from a hybridization made in October 2017 in a greenhouse in Gilroy, Calif. The female parent was the unpatented, proprietary plant designated as 'B9327', having smaller decorative inflorescences, shorter less vigorous growth habit and weaker plant strength when compared to 'CIDZ0115'.

The male parent of 'CIDZ0115' was the unpatented, proprietary plant designated as 'C0151', having yellow semi-double type inflorescences with abundant pollen production, and more vigorous growth habit than 'CIDZ0115'.

The seed was sown in July 2018 and the resulting plants were grown out of doors in a field covered by saran cloth in Fort Myers, Fla. 'CIDZ0115' was selected as one flowering plant within the progeny of the stated cross in December 2018.

The first act of asexual reproduction of 'CIDZ0115' was accomplished when vegetative cuttings were propagated from the initial selection in March 2019 in Gilroy Calif.

BRIEF SUMMARY OF INVENTION

Horticultural examination of plants grown from cuttings of the plant initiated in March 2019 and continuing thereafter, has demonstrated that the combination of characteristics as herein disclosed for 'CIDZ0115' are firmly fixed and are retained through successive generations of asexual reproduction.

'CIDZ0115' has not been observed under all possible environmental conditions. The phenotype may vary significantly with variations in environment such as temperature, light intensity and day length.

A Plant Breeder's Right for this cultivar was applied for in Canada on Oct. 21, 2022, No. 22-11111. 'CIDZ0115' has not been made publicly available prior to the effective filing date of this application, notwithstanding any disclosure that may have been made less than one year prior to the effective filing date of this application by the inventor or another who obtained 'CIDZ0115' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0115' with colors being as true as possible with an illustration of this type. The photographic drawings show in FIG. 1 a close-up view of an inflorescence, and in FIG. 2 a flowering plant of the new variety.

DETAILED BOTANICAL DESCRIPTION

The plant descriptions and measurements were taken indoors in Gilroy, Calif. in August 2022 on about 11 week old plants. Unrooted cuttings had been planted, 4 plants per pot, in 6 inch pots in May 2022. The plants were pinched and moved to short days in June 2022 to induce flowering.

Figure 2:
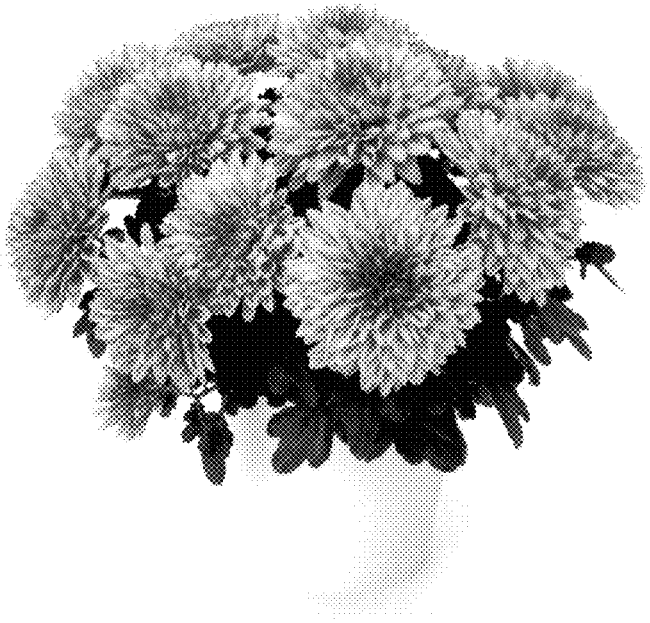

The aforementioned photographs: FIGS. 1 and 2 was taken in Gilroy, Calif. in May 2022, and showing a plant from a trial, in which flowering had been induced by applying black cloth. These plants were about 11 weeks of age. Unrooted cuttings had been planted, 4 plants per pot, in 6 inch pots. The plants were pinched and moved to short days to induce flowering.

Color references are made to The Royal Horticultural Society Colour Chart (R.H.S.) 2001.

TABLE 1

DIFFERENCES BETWEEN THE NEW VARIETY 'CIDZ0115' AND A MOST SIMILAR VARIETY:

| | 'CIDZ0115' | 'Deep Yopresidio', U.S. Plant Pat. No. 17,493 |
|---|---|---|
| Plant habit: | Wider branching | More upright |
| Plant height: | Shorter | Taller |
| Flower size: | Smaller | Larger |

Plant:

*Form, growth and habit.*—Herbaceous pot-type, stems upright to moderately angled, freely branching, strong and compact growth habit.

*Plant height.*—29.0 cm.

*Plant height (inflorescence included).*—36.0 cm.

*Plant width.*—47.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 137C.

*Lower surface.*—RHS 138B.

*Mature, leaf color, upper surface.*—RHS 139A.

*Lower surface.*—RHS 137B.

*Length.*—6.8-9.1 cm.

*Width.*—3.9-6.1 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Puberlulent.

*Lower surface.*—Puberlulent.

*Color of veins, upper surface.*—RHS 138D.

*Color of veins, lower surface.*—RHS 138D.

*Pattern of veining.*—Palmate.

*Petiole color.*—RHS 139A.

*Length.*—1.0-1.7 cm.

*Diameter.*—0.2-0.6 cm.

*Texture.*—Puberlulent.

Stem:

*Quantity of main branches per plant.*—4-5.

*Color of stem.*—RHS 138C.

*Length of stem.*—23.0-25.0 cm.

*Diameter.*—0.6-0.7 cm.

*Length of internodes.*—0.2-3.4 cm.

*Texture.*—Puberlulent.

*Color of peduncle.*—RHS 138C.

*Length of peduncle.*—4.0-11.0 cm.

*Peduncle diameter.*—0.2 cm.

*Texture.*—Puberlulent.

*Stipule color.*—RHS 137A.

*Stipule length.*—0.6-0.9 cm.

*Stipule width.*—0.9-1.1 cm.

Inflorescence:

*Type.*—Compositae type, double-type inflorescences borne terminally above foliage, ray florets arranged acropetally on a capitulum.

*Quantity of short days to flowering (response time).*—7.5 weeks.

*Natural season flowering.*—Not determined for this variety.

*Quantity of inflorescences per plant.*—Average of 5 for disbudded plants.

*Lastingness of individual blooms on the plant.*—4 weeks.

*Fragrance.*—Slightly spicy.

Bud (just when opening/showing color):

*Color.*—RHS 72A.

*Length.*—1.2 cm.

*Width.*—1.1 cm.

*Shape.*—Oblate.

Immature inflorescence:

*Diameter.*—4.8 cm.

*Color of ray florets, upper surface.*—Closest to RHS 72B.

*Lower surface.*—Closest to RHS 72B and tones of RHS 155C.

Mature inflorescence:

*Diameter.*—9.0-10.0 cm.

*Depth.*—2.8-3.0 cm.

*Total diameter of disc.*—0.2 cm.

*Receptacle color.*—RHS 145C.

*Receptacle height.*—0.25 cm.

*Receptacle diameter.*—0.6 cm.

Ray florets:

*Average quantity of florets.*—Average of 239.

*Color of florets, upper surface.*—Closest to RHS 72B and RHS 155D.

*Lower surface.*—Closest to RHS 72B and RHS 155D.

*Length.*—4.1-4.5 cm.

*Width.*—1.5-1.7 cm.

*Shape.*—Elliptical.

*Shape at longitudinal axis.*—Straight.

*Apex shape.*—Mucronulate.

*Margin.*—Entire.

*Length of corolla tube.*—Short.

*Texture, upper surface.*—Papillose.

*Lower surface.*—Papillose.

Disc florets:

*Average quantity of florets.*—7.

*Color of florets.*—RHS 13A.

*Length.*—0.4 cm.

*Width.*—0.1 cm.

*Shape.*—Tubular, elongated.

*Apex shape.*—Acute, 5 pointed.

Phyllaries:

*Quantity.*—Average of 28.

*Color, upper surface.*—RHS 137A.

*Lower surface.*—RHS 137A.

*Length.*—0.9-1.0 cm.

*Width.*—0.3-0.5 cm.

*Shape.*—Lanceolate.

*Apex shape.*—Acute.

*Base.*—Fused.

*Margins.*—Entire; papery.

*Texture, upper surface.*—Glabrous.

*Lower surface.*—Puberlulent.

Reproductive organs:

*Pistil.*—1, found on both types of florets.
*Length.*—0.55 cm.
*Style color.*—RHS 145D.
*Style length.*—0.5 cm.
*Stigma color.*—RHS 1C.
*Stigma shape.*—Bi-parted.
*Ovary color.*—RHS 155C but more translucent.
*Stamens.*—4, found on only on the disc florets.
*Color of filaments.*—RHS 155C.
*Length filaments.*—0.2 cm.
*Anther color.*—RHS 12A.
*Anther length.*—0.15 cm.
*Anther shape.*—Oval.
*Color of pollen.*—RHS 12A.
*Pollen amount.*—Very little.
*Fertility/seed set.*—Unknown.
*Disease/pest resistance.*—Has not been observed to date.
*Plant hardiness.*—Has not been observed to date.

What is claimed is:

1. A new and distinct variety of *Chrysanthemum* plant named 'CIDZ0115' substantially as illustrated and described herein.

* * * * *